United States Patent [19]

Yoshihara et al.

[11] Patent Number: 5,242,689
[45] Date of Patent: Sep. 7, 1993

[54] COSMETIC COMPOSITION

[75] Inventors: Toru Yoshihara; Jiro Kawase, both of Tokyo, Japan

[73] Assignee: KAO Corporation, Tokyo, Japan

[21] Appl. No.: 694,999

[22] Filed: May 2, 1991

[30] Foreign Application Priority Data

Jun. 5, 1990 [JP] Japan .................. 2-146598

[51] Int. Cl.$^5$ .................. A61K 7/021; A61K 7/13
[52] U.S. Cl. .................. 424/401; 424/63; 424/69; 424/70; 106/499; 106/502; 428/403; 428/407
[58] Field of Search .................. 424/401, 63, 69, 70, 424/78, 62; 106/472, 476, 478, 493; 428/403, 404, 407

[56] References Cited

U.S. PATENT DOCUMENTS

| | | | |
|---|---|---|---|
| 3,697,643 | 10/1972 | Shepard et al. | 424/70 |
| 4,536,405 | 8/1985 | Nara et al. | 424/63 |
| 4,711,833 | 12/1987 | McAneney et al. | 430/131 |
| 4,806,360 | 2/1989 | Leong et al. | 424/486 |
| 4,820,510 | 4/1989 | Arraudeau et al. | 424/63 |
| 4,820,518 | 4/1989 | Murphy et al. | 424/63 |
| 4,828,826 | 5/1989 | Franz et al. | 424/69 |
| 4,937,060 | 6/1990 | Kathirgamanathan | 428/403 |
| 4,948,690 | 8/1990 | Hisamura et al. | 430/64 |
| 5,057,370 | 10/1991 | Krieg et al. | 428/407 |

FOREIGN PATENT DOCUMENTS 2207153  1/1989 United Kingdom .

Primary Examiner—Thurman K. Page
Assistant Examiner—Amy Hulina
Attorney, Agent, or Firm—Birch, Stewart, Kolasch & Birch

[57] ABSTRACT

A cosmetic composition comprising fine particles coated with Pyrrole Black.

6 Claims, No Drawings

COSMETIC COMPOSITION

BACKGROUND OF THE INVENTION

1. Field of the Invention

The present invention relates to a cosmetic composition comprising a specified black pigment and a cosmetic composition comprising the black pigment and an oil component. The cosmetic composition of the present invention is suitably usable as a composition for temporarily dyeing the hair or a makeup composition for the eyelashes, eyebrows and skin.

2. Description of the Prior Art

Ordinary compositions for dyeing the hair and makeup compositions for the eyelashes, eyebrows and skin contain carbon black or a black or brown pigment mainly comprising a metal oxide such as an iron oxide. However, it is known that the carbon black contains highly carcinogenic benzpyrene and, in addition, the metal oxides have problems that the blackness thereof is low, that its covering effect is insufficient and that its specific gravity is high. Under these circumstances, there have been various attempts to develop a black pigment harmless to the human body and having a high blackness (i.e. high covering effect). For example, Japanese Patent Laid-Open No. 92273/1989 discloses a cosmetic composition comprising fine inorganic particles coated with a black pigment prepared by oxidative polymerization of 5,6-dihydroxyindole which is a melanin precursor with hydrogen peroxide, a periodate or a transition metal salt. U.S. Pat. No. 4,806,360 discloses a synthetic melanin aggregate prepared by oxidative polymerization of a melanin precursor such as dopa in a polymer network of a porous polymer.

However, the cosmetic composition disclosed in the Japanese Patent Laid-Open No. 92273/1989 is not easy to prepare in practice, since 5,6-dihydroxyindole used as the starting material for the black pigment is a quite unstable compound. The color tone of the synthetic melanin aggregate disclosed in the U.S. Pat. No. 4,806,360 is browny black or reddish black so that its blackness is low.

SUMMARY OF THE INVENTION

An object of the present invention is to provide a cosmetic composition which is harmless to the human bodies, has a sufficiently high blackness and can be relatively easily synthesized.

After intensive investigations made for the purpose of attaining the above-described object, the inventors have found that a black pigment comprising fine particles coated with pyrrole which is negative in the mutagenicity test by oxidative polymerization has a sufficiently high blackness, is utterly harmless to the human bodies and is relatively easily synthesized. The inventors have found also that since the surface of the black pigment is made hydrophobic by Pyrrole Black, it has a high affinity for oil components which are usually accepted as cosmetic ingredients and, therefore, when the pigment is used in combination with the oil components, sufficiently high covering effect, smoothness and spreadability can be obtained.

The present invention has been completed on the basis of these findings and provides a cosmetic composition characterized by comprising fine particles coated with a pyrrole homopolymer, i.e. Pyrrole Black.

The present invention provides also a cosmetic composition characterized by comprising the fine particles coated with Pyrrole Black and an oil component.

The cosmetic composition of the present invention comprising the black pigment which is harmless to the human bodies, has a sufficiently high blackness and can be relatively easily synthesized is suitably usable as a composition for temporarily dyeing the hair or a makeup composition for the eyelashes, eyebrows and skin. It is smooth, highly spreadable and easily usable.

DETAILED DESCRIPTION OF THE INVENTION

The fine particles (black pigment) coated with Pyrrole Black to be used in the present invention can be produced by a process described in A. Yassar et al., Polymer Communications, 28, 103–104 (1987). In particular, they can be produced by dissolving pyrrole in, for example, water or a lower alcohol, dispersing the fine particles in the solution and adding dropwise an aqueous solution of a ferric salt to form a difficulty soluble Pyrrole Black layer on the fine particle surface. The black pigment thus produced is isolated by filtration, washing with water, washing with ethanol, washing with acetone, and drying. In this process for producing the black pigment, the weight ratio of pyrrole to the fine particles is preferably 0.05/1 to 10/1, still preferably 0.1/1 to 5/1, and that of the ferric salt to the fine particles is preferably 0.5/1 to 20/1, still preferably 1.0/1 to 10/1. The weight ratio of pyrrole to the ferric salt is preferably 5/1 to 1/5 and still preferably 3/1 to 1/3. When the content of the ferric salt is below the above-described range, no black pigment having a sufficient blackness can be obtained. On the contrary, even when it is above the above-described range, the blackness can no more be improved.

The fine particles to be coated with Pyrrole Black may be a powder of an inorganic substance or an organic substance. Examples of the inorganic substances include clays such as talc and kaolin, calcium carbonate, titanium oxide and silica. The organic substances are preferably synthetic polymers, more specifically hydrocarbon polymers such as polyethylene, polypropylene and polystyrene; polyamide polymers such as nylon; vinyl polymers such as polyvinyl chloride, polyacrylonitrile, polyacrylic acid, polyacrylic esters, polymethacrylic acid, polymethacrylic esters and polyvinyl acetate; polyester polymers, and polyurethane polymers, as well as copolymers and crosslinked polymers of them. The diameter of the fine particle before the coating varies depending on the type of the formulation. It is preferably 0.01 to 200 μm under an electron microscope. Since pyrrole is coated into Pyrrole Black by the oxidative polymerization to form a black coating on the surface of an arbitrarily selected fine particle, it is capable of forming a useful black pigment from an inorganic powder usually used as a cosmetic powder or from a synthetic polymer which can be shaped into any desired shape. Thus a black pigment having any desired specific gravity can be produced.

The fine particle (black pigment) having a surface coated with Pyrrole Black has a strong covering effect and a hydrophobic surface and is highly compatible with oil components usually contained in cosmetics. Accordingly, when this pigment is used in combination with these components, a cosmetic having a sufficiently high covering effect, high smoothness and excellent spredability can be obtained.

The amount of the black pigment used varies depending on the use and type of the cosmetic composition. It is usually preferably 0.1 to 50% by weight, still preferably 0.3 to 30% by weight, based on the cosmetic composition.

The oil components used in the present invention include oils and waxes usually incorporated into cosmetics.

The oils include hydrocarbons such as liquid paraffin, squalane, isopropyl myristate and isopropyl palmitate; animal oils such as mink oil; vegetable oils such as cotton seed oil, olive oil, tsubaki oil, coconut oil, soybean oil, sesame oil, cacao butter and castor oil; silicone derivatives such as methylpolysiloxane, methylphenylpolysiloxane, silicone polyether copolyer, amino-modified silicone, methylpolycyclosiloxane, cyclic silicone and silicone polymer; ester oils such as octyldodecyl myristate; and ether oils such as isostearyl glyceryl ether.

The waxes include solid oils such as beeswax, spermaceti, lanolin, solid paraffin, microcrystalline way, vaseline, Japan wax, carnauba wax and candelilla wax. They are heat melted and mixed with the fine particles.

The amount of the oil component which varies depending on the type of the final product is preferably 0.1 to 70% by weight, still preferably 0.2 to 50% by weight, based on the cosmetic composition.

The weight ratio of the oil component to the black pigment is preferably 100/1 to 1/10 and still preferably 50/1 to 1/50.

The cosmetic composition of the present invention is usable as a hair dyeing composition such as a temporary hair dye of mascara type, spray type of foam type; or as a makeup composition for the eyelashes, eyebrows and skin, such as an eye shadow, cheek rouge, eye liner and mascara for the eyelashes or eyebrows.

The cosmetic composition of the present invention is usable in the form of a lotion, thickened lotion, gel, cream, powder, compressed powder or stick. If desired, it is usable in combination with a propellant to form a spray or foam.

The cosmetic composition of the present invention may contain additives which can be usually added to such cosmetics depending on the use so far as the effect of the present invention is not impaired. The additives include anionic, nonionic, cationic and amphoteric surfactants, organic solvents, thickening agents, emollients, flavors, preservatives, antioxidants, fillers, sequestering agents, anionic, cationic, nonionic and amphoteric polymers and mixtures of them, alkalinizing agents or acidifying agents, and other pigments usually used for cosmetics, particularly, pearly pigments capable of changing the color tone.

The cosmetic composition of the present invention is used as a temporary hair-dyeing composition or as a makeup composition for the eyelashes, eyebrows and skin. The composition has excellent smoothness and spreadability and is harmless and highly safe. It dyes the hair, eyelashes and eyebrows black to exhibit a high covering effect.

The following Synthesis Examples for the black pigment as the constituent of the present invention and Examples will further illustrate the present invention, which by no means limit the invention.

SYNTHESIS EXAMPLE 1

3 g of pyrrole was dissolved in 70 g of a 40% aqueous ethanol solution. Then 1 g of titanium oxide was dispersed in the solution and 30 g of a 20% aqueous ferric chloride solution was added dropwise thereto under thorough stirring for 15 min. After the completion of the addition, the stirring was continued for additional one hour. After filtration followed by washing with water, washing with ethanol, washing with acetone and drying, 2.1 g of a black powder (black pigment)(secondary particle diameter: 5 to 10 μm) was obtained.

SYNTHESIS EXAMPLE 2

3 g of pyrrole was dissolved in 70 g of a 40% aqueous ethanol solution. Then 1 g of a styrene/stearyl methacrylate/divinylbenzene copolymer was dispersed in the solution and 30 g of 20% aqueous ferric chloride solution was added dropwise thereto under thorough stirring for 15 min. After the completion of the addition, the stirring was continued for additional one hour. After filtration followed by washing with water, washing with ethanol, washing with acetone and drying, 2.0 g of a black powder (black pigment)(secondary particle diameter: 5 to 10 μm) was obtained.

Each of the black pigments obtained in Synthesis Examples 1 and 2 was incorporated into liquid paraffin and placed in a frame having a diameter of 3 cm to evaluate the blackness with the naked eyes. For comparison, the blackness of each of black iron oxide (Comparative Example 1) and a black pigment (Comparative Example 2) produced in the same manner as that described in Example 3 of U.S. Pat. No. 4,806,360 was also determined in the same manner. The results are given in the following Table.

| Synthesis Example 1 | Synthesis Example 2 | Comparative Example 1 | Comparative Example 2 |
| --- | --- | --- | --- |
| deep black | deep black | intensely reddish black | reddish black |

EXAMPLE 1

The following temporary hair dyeing composition of mascara type was prepared.

| [Formulation] | |
| --- | --- |
| black pigment prepared in Synthesis Example 2 | 4.0 g |
| amphoteric polymer (Plascize K-53D for color toner A*1) | 4.0 g |
| silicone polyether copolymer (Silicone SH 377X*2) | 0.2 g |
| nonionic surfactant (Softanol 90*3) | 1.0 g |
| ethanol | 25.0 g |
| water | the balance |
| | 100.0 g |

*1 a product of Goo Chemical Industries Co., Ltd.
*2 a product of Toray Silicone Co., Ltd.
*3 a product of Nippon Shokubai Kagaku Kogyo Co., Ltd.

The composition thus obtained sufficiently covered the gray hair.

EXAMPLE 2

The following temporary hair dye composition of spray type was prepared:

| [Formulation] | |
| --- | --- |
| black pigment prepared in Synthesis Example 2 | 0.3 g |
| anionic polymer (Plascize L-53D for color toner A*4) | 1.0 g |
| methylpolysiloxane (Silicone SH 200*5) | 0.2 g |

-continued

| [Formulation] | |
|---|---|
| ethanol | 37.7 g |
| nonionic surfactant (Softanol 90) | 1.0 g |
| chlorofluorocarbon gas (11/12–40/60) | 60.0 g |
| | 100.0 g |

*4 a product of Goo Chemical Industries Co., Ltd.
*5 a product of Toray Silicone Co., Ltd.

The composition thus obtained sufficiently covered the gray hair.

EXAMPLE 3

The following temporary hair dye composition of foam type was prepared:

| [Formulation] | |
|---|---|
| black pigment prepared in Synthesis Example 2 | 1.0 g |
| amphoteric polymer(Yuka Foamer AM75R*6) | 4.0 g |
| ethanol | 5.0 g |
| nonionic surfactant (Softanol 90) | 1.0 g |
| liquefied petroleum gas | 10.0 g |
| nonionic surfactant (Emanon 3299R*7) | 0.5 g |
| water | the balance |
| | 100.0 g |

*6 a product of Mitsubishi Petrochemical Co., Ltd.
*7 a product of Kao Corporation.

The composition thus obtained sufficiently covered the gray hair.

EXAMPLE 4

The following eyeliner composition of pencil type was prepared:

| [Formulation] | |
|---|---|
| black pigment prepared in Synthesis Example 2 | 30.0 g |
| hydrogenated castor oil | 10.0 g |
| stearic acid | 10.0 g |
| Japan wax | 5.0 g |
| vaseline | 20.0 g |
| liquid paraffin | 15.0 g |
| pearly agent | 10.0 g |
| | 100.0 g |

The composition thus obtained had excellent smoothness and spreadability and a sufficient blackness.

EXAMPLE 5

The following solid mascara composition was prepared:

| [Formulation] | |
|---|---|
| stearic acid triethanolamide | 26.0 g |
| black pigment prepared in Synthesis Example 1 | 18.0 g |
| beeswax | 17.0 g |
| solid paraffin | 26.0 g |
| lanolin | 10.0 g |
| carnauba wax | 3.0 g |
| | 100.0 g |

The composition thus obtained had excellent smoothness and spreadability and a sufficient blackness.

What is claimed is:

1. A cosmetic composition comprising organic particles having a diameter of between 0.01 to 200 μm coated with polypyrrole, and a cosmetically acceptable oil or wax.

2. A cosmetic composition according to claim 1 wherein said particle comprises a powdery organic substance selected from the group consisting of polyethylene, polypropylene, polystyrene, nylon, polyvinyl chloride, polyacrylonitrile, polyacrylic acid, polyacrylic ester, polymethacrylic acid, polymethacrylic ester, and polyvinyl acetate; or a copolymer or crosslinked polymer thereof.

3. A cosmetic composition according to claim 1 or 2 wherein the amount of said particles coated with polypyrrole is 0.1 to 50% by weight based on the cosmetic composition.

4. A cosmetic composition according to claim 1 wherein the amount of said cosmetically acceptable oil or wax is 0.1 to 70% by weight based on the cosmetic composition.

5. The cosmetic composition according to claim 1 wherein the weight ratio of said cosmetically acceptable oil or wax to said particles coated with polypyrrole is 100/1 to 1/100.

6. The cosmetic composition according to claim 1, wherein said organic particle comprises a styrene/stearyl methacrylate/divinylbenzene copolymer.

* * * * *